(12) United States Patent
Orbay

(10) Patent No.: US 6,893,444 B2
(45) Date of Patent: May 17, 2005

(54) BONE FRACTURE FIXATION SYSTEMS WITH BOTH MULTIDIRECTIONAL AND UNIDIRECTIONAL STABILIZATION PEGS

(75) Inventor: Jorge L. Orbay, Miami, FL (US)

(73) Assignee: Hand Innovations, LLC, Miami, FL (US)

(*) Notice: Subject to any disclaimer, the term of this patent is extended or adjusted under 35 U.S.C. 154(b) by 99 days.

(21) Appl. No.: 10/307,796

(22) Filed: Dec. 2, 2002

(65) Prior Publication Data

US 2003/0083660 A1 May 1, 2003

Related U.S. Application Data

(63) Continuation-in-part of application No. 10/159,611, filed on May 30, 2002, now Pat. No. 6,730,090, and a continuation-in-part of application No. 10/159,612, filed on May 30, 2002, now Pat. No. 6,767,351, which is a continuation-in-part of application No. 09/735,228, filed on Dec. 12, 2000, now Pat. No. 6,440,135, which is a continuation-in-part of application No. 09/524,058, filed on Mar. 13, 2000, now Pat. No. 6,364,882, and a continuation-in-part of application No. 09/495,854, filed on Feb. 1, 2000, now Pat. No. 6,358,250.

(51) Int. Cl.$^7$ .............................................. A61B 17/80
(52) U.S. Cl. .................................................... 606/69
(58) Field of Search ..................... 606/69–73

(56) References Cited

U.S. PATENT DOCUMENTS

| | | |
|---|---|---|
| 3,741,205 A | 6/1973 | Markolf et al. |
| RE28,841 E | 6/1976 | Allgower et al. |
| 4,172,452 A | 10/1979 | Forte et al. |
| 4,408,601 A | 10/1983 | Wenk |
| 4,493,317 A | 1/1985 | Klaue |
| 4,506,662 A | 3/1985 | Anapliotis |
| 4,794,919 A | 1/1989 | Nilsson |
| 4,867,144 A | 9/1989 | Karas et al. |
| 5,006,120 A | 4/1991 | Carter |
| 5,013,314 A | 5/1991 | Firica et al. |
| 5,015,248 A | 5/1991 | Burstein et al. |
| 5,041,113 A | 8/1991 | Biedermann et al. |

(Continued)

OTHER PUBLICATIONS

*Polyaxial and Monoaxial Spinal Screws*, XIA™ Spinal System, www.osteonics.com/osteonics/spine/xia2.html, Aug. 15, 2000.
"Summary of Safety and Effectiveness Information"; Synthes®; Jul. 29, 1998.
"The Distal Radius Plate Instrument and Implant Set", Technique Guide, SYNTHES®, Paoli, PA 1995.
"The Titanium Distal Radius Plate", Technique Guide, SYNTHES®, Paoli, PA, 1995.
"SCS™/D Distal Radius Plate System: Dorsal", Avanta 1997.
"SCS™/V Distal Radius Plate: Volar", Avanta 1998.
"Advances in distal Radius Fracture Management (D)", transcript of American Academy of Orthopaedic Surgeons 2001 Conf.; pp. 134–151, Feb. 28, 2001 including Article by Matthew D. Putnam MD, "Repair and Rehabilitation of Distal Fractures: The Role of Subchondral Fixation" at pp. 144–147.

*Primary Examiner*—Kevin Shaver
*Assistant Examiner*—Michael B. Priddy
(74) *Attorney, Agent, or Firm*—Gordon & Jacobson, PC

(57) ABSTRACT

A fixation system includes a device having a plurality of like threaded peg holes. Two types of pegs are couplable within the peg holes. One type is multidirectional, and the shaft can be oriented at various angles relative to an axis extending through the peg hole. Another peg is directionally-fixed and limited to extension through the peg hole in a single direction; i.e., coaxial with the peg hole axis. The peg holes and both types of pegs are adapted such that either of the pegs can be received within any of the peg holes of the device.

39 Claims, 9 Drawing Sheets

U.S. PATENT DOCUMENTS

| | | | |
|---|---|---|---|
| 5,127,912 A | * 7/1992 | Ray et al. | 606/61 |
| 5,151,103 A | 9/1992 | Tepic et al. | |
| 5,382,248 A | 1/1995 | Jacobson et al. | |
| 5,472,444 A | 12/1995 | Huebner et al. | |
| 5,531,745 A | 7/1996 | Ray | |
| 5,549,612 A | 8/1996 | Yapp et al. | |
| 5,603,715 A | 2/1997 | Kessler | |
| 5,676,667 A | 10/1997 | Hausman | |
| 5,709,686 A | 1/1998 | Talos et al. | |
| 5,718,705 A | 2/1998 | Sammarco | |
| 5,853,413 A | 12/1998 | Carter et al. | |
| 5,879,350 A | 3/1999 | Sherman et al. | |
| 5,931,839 A | 8/1999 | Medoff | |
| 5,989,254 A | 11/1999 | Katz | |
| 6,010,503 A | 1/2000 | Richelsoph et al. | |
| 6,022,350 A | * 2/2000 | Ganem | 606/61 |
| 6,096,040 A | 8/2000 | Esser | |
| 6,146,384 A | 11/2000 | Lee et al. | |
| 6,197,028 B1 | 3/2001 | Ray et al. | |
| 6,221,073 B1 | 4/2001 | Weiss et al. | |
| 6,270,499 B1 | 8/2001 | Leu et al. | |
| 6,283,969 B1 | 9/2001 | Grusin et al. | |
| 6,355,041 B1 | 3/2002 | Martin | |
| 6,379,359 B1 | 4/2002 | Dahners | |
| 6,409,768 B1 | 6/2002 | Tepic et al. | |
| 6,527,775 B1 | 3/2003 | Warburton | |
| 6,595,993 B2 | * 7/2003 | Donno et al. | 606/71 |
| 6,623,486 B1 | * 9/2003 | Weaver et al. | 606/69 |
| 6,626,908 B2 | * 9/2003 | Cooper et al. | 606/61 |
| 2001/0001119 A1 | * 5/2001 | Lombardo | 606/73 |
| 2003/0105461 A1 | 6/2003 | Putnam | |

* cited by examiner

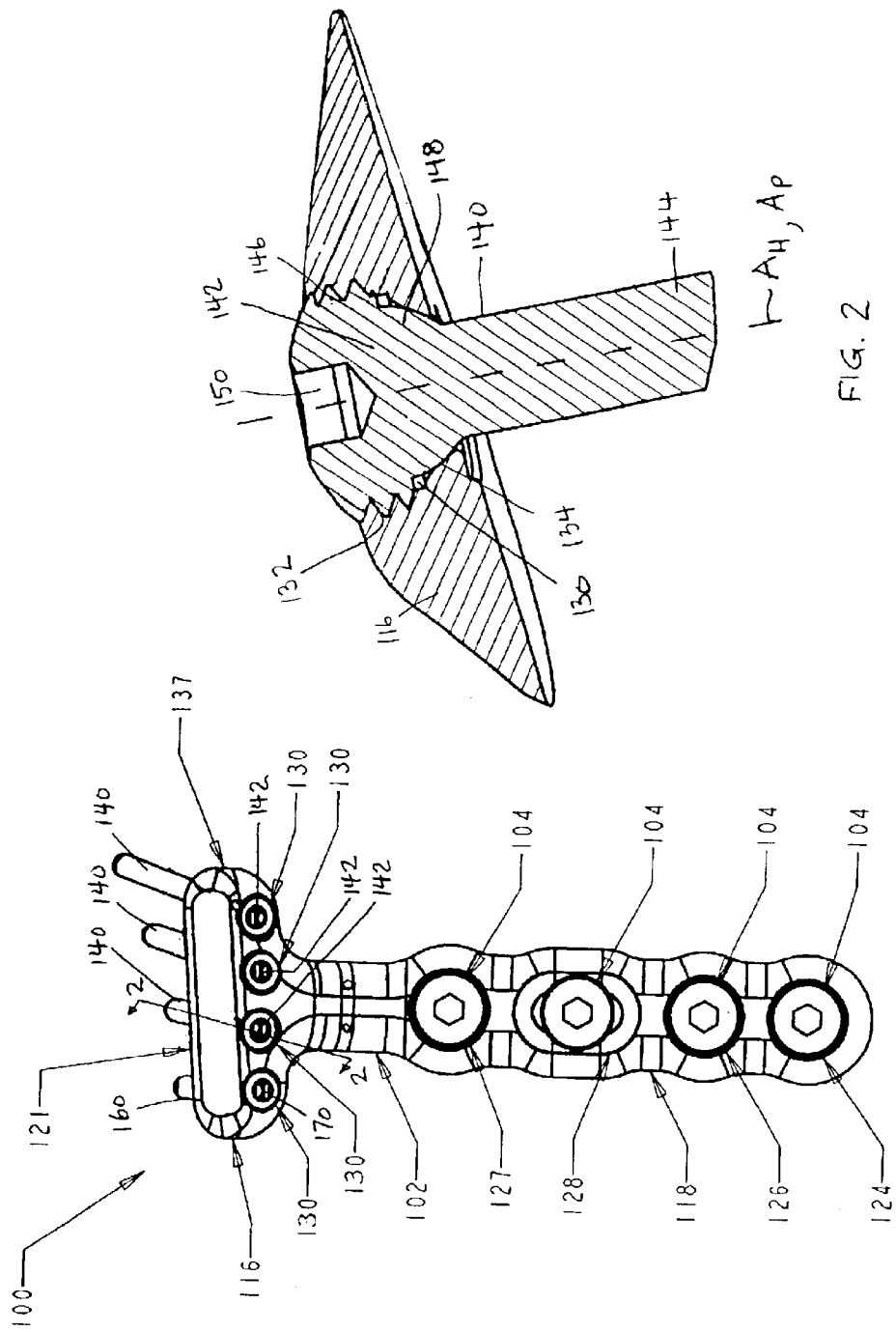

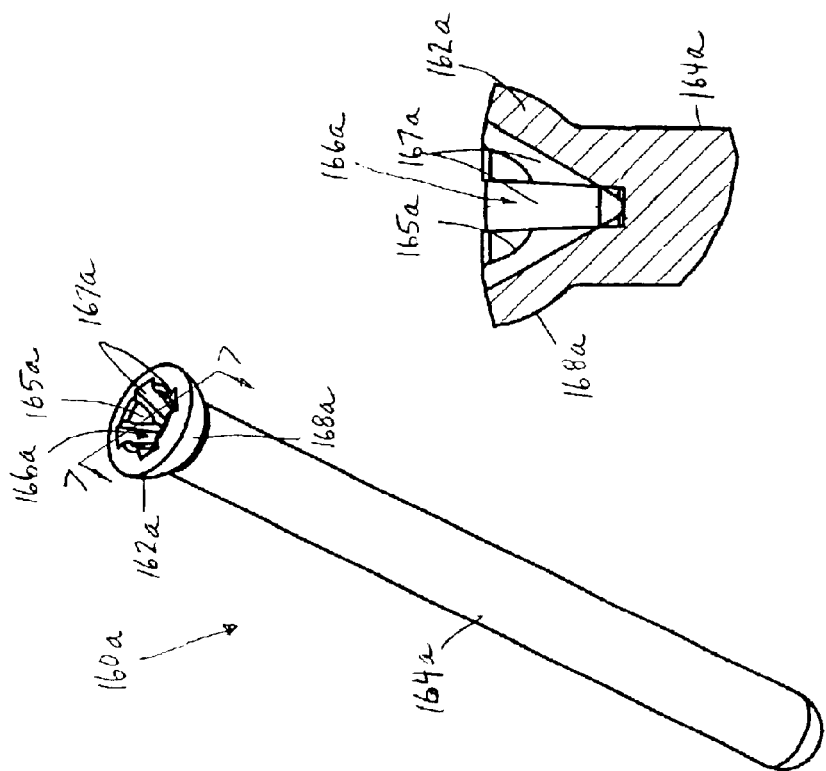
FIG. 6
FIG. 7
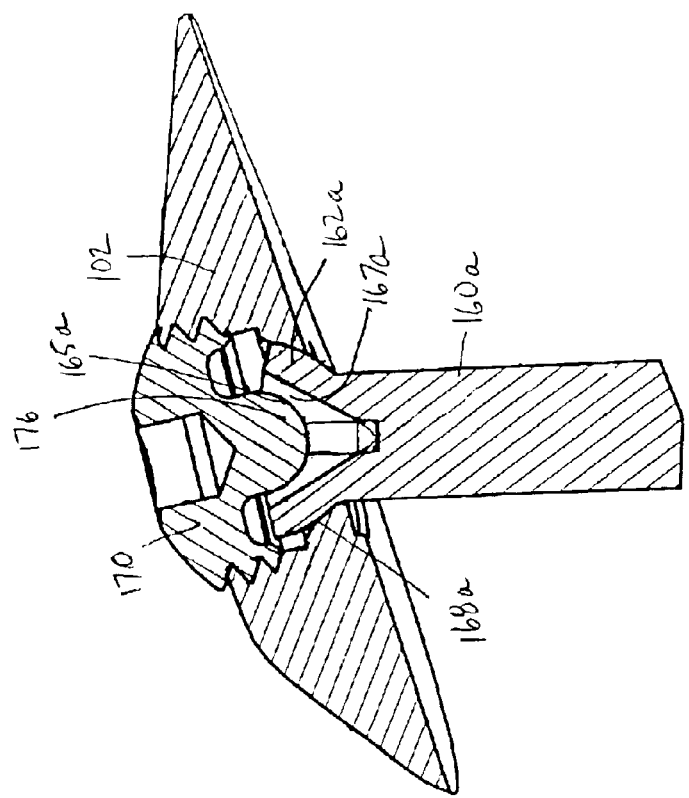
FIG. 5

BONE FRACTURE FIXATION SYSTEMS WITH BOTH MULTIDIRECTIONAL AND UNIDIRECTIONAL STABILIZATION PEGS

This application is a continuation-in-part of both U.S. Ser. No. 10/159,611, filed May 30, 2002, now U.S. Pat. No. 6,730,090, and U.S. Ser. No. 10/159,612, filed May 30, 2002, now U.S. Pat. No. 6,767,351, which are each continuations-in-part of U.S. Ser. No. 09/735,228, filed Dec. 12, 2000, now U.S. Pat. No. 6,440,135, which is a continuation-in-part of both U.S. Ser. No. 09/524,058, filed Mar. 13, 2000, now U.S. Pat No. 6,364,882 and U.S. Ser. No. 09/495,854, filed Feb. 1, 2000, now U.S. Pat No. 6,358,250, all of which are hereby incorporated by reference herein in their entireties.

BACKGROUND OF THE INVENTION

1. Field of the Invention

This invention relates broadly to surgical devices. More particularly, this invention relates to a bone fixation system having support pegs.

2. State of the Art

Fracture to the metaphyseal portion of a long bone can be difficult to treat. Improper treatment can result in deformity and long-term discomfort.

By way of example, a Colles' fracture is a fracture resulting from compressive forces being placed on the distal radius, and which causes backward displacement of the distal fragment and radial deviation of the hand at the wrist. Often, a Colles' fracture will result in multiple bone fragments which are movable and out of alignment relative to each other. If not properly treated, such fractures result in permanent wrist deformity. It is therefore important to align the fracture and fixate the bones relative to each other so that proper healing may occur.

Alignment and fixation of a metaphyseal fracture are typically performed by one of several methods: casting, external fixation, interosseous wiring, and plating. Casting is non-invasive, but may not be able to maintain alignment of the fracture where many bone fragments exist. Therefore, as an alternative, external fixators may be used. External fixators utilize a method known as ligamentotaxis, which provides distraction forces across the joint and permits the fracture to be aligned based upon the tension placed on the surrounding ligaments. However, while external fixators can maintain the position of the wrist bones, it may nevertheless be difficult in certain fractures to first provide the bones in proper alignment. In addition, external fixators are often not suitable for fractures resulting in multiple bone fragments. Interosseous wiring is an invasive procedure whereby screws are positioned into the various fragments and the screws are then wired together as bracing. This is a difficult and time-consuming procedure. Moreover, unless the bracing is quite complex, the fracture may not be properly stabilized. Plating utilizes a stabilizing metal plate typically against the dorsal side of the bones, and a set of parallel pins extending from the plate into holes drilled in the bone fragments to provide stabilized fixation of the fragments. However, the currently available plate systems fail to provide desirable alignment and stabilization. Similar problems regarding fracture stabilization are present in non-metaphyseal fractures, as well.

SUMMARY OF THE INVENTION

It is therefore an object of the invention to provide an improved fixation and stabilization system for bone fractures.

It is another object of the invention to provide an improved fixation and stabilization system for metaphyseal bone fractures.

It is also an object of the invention to provide a fixation and stabilization system that desirably aligns and stabilizes multiple bone fragments in a fracture to permit proper healing.

It is a further object of the invention to provide a fixation and stabilization system that is highly adjustable to provide a customizable framework for bone fragment stabilization.

It is an additional object of the invention to provide a fixation and stabilization system that is relatively easy to implant.

In accord with these objects, which will be discussed in detail below, a fracture fixation and stabilization system is provided which generally includes a device intended to be positioned against a non-fragmented portion of a fractured bone, one or more bone screws for securing the device along the non-fragmented portion of the bone, and a plurality of bone pegs coupled to the device and extending therefrom into bone fragments adjacent the non-fragmented portion.

According to the invention, the device includes a plurality of threaded peg holes adapted to receive the pegs therethrough. The peg holes include an upper internally threaded portion, and a lower spherically concave surface. In accord with the invention, two types of pegs are provided for insertion through the threaded peg holes, and the peg holes and the pegs are adapted such that either type of peg can be used in any one of the peg holes of the device.

The first type of peg includes a head and a shaft, with the head having an upper externally threaded portion adapted to engage the threads of the peg hole, a lower spherically convex portion, and a driver receiving means, such as a proximal hex socket. Pegs of the first type can be threadably engaged within the peg holes of the plate to extend in alignment with axes through respective peg holes; i.e., the first type of pegs are unidirectional or fixed-directional.

The second type of peg includes a head and shaft, with the head defining an upper cup and an outer spherically convex portion. The second type of peg is adapted to operate in conjunction with a cap having an externally threaded portion adapted to engage within the threaded portion of the peg hole, a driver receiving means, and a lower preferably spherically curved ball portion (or nub) sized to be at least partially received within the cup. A peg of the second type can be inserted through any peg hole and oriented in any angle within a permitted range of angles relative to the axis of the peg hole. The cap is then inserted into the peg hole and tightened to clamp the head of the peg between the cap and the lower concave surface surrounding the peg hole. As such, the second type of pegs can be independently fixed in a selectable orientation; i.e., the pegs are multidirectional.

This system is adaptable to substantially any fixation system that can use stabilization pegs. For example, volar plates; nail-plate systems for the distal radius, ulna, femur, and tibia; shoulder plates; humeral plates; etc., can all be provided as a system adapted to use by unidirectional and multidirectional pegs.

Additional objects and advantages of the invention will become apparent to those skilled in the art upon reference to the detailed description taken in conjunction with the provided figures.

BRIEF DESCRIPTION OF THE DRAWINGS

FIG. 1 is a top view of a volar fixation system according to a first embodiment of the system of the invention;

FIG. 2 is a section view of a head portion of the volar fixation system according to the invention, showing a unidirectional fixed-angle peg inserted in a peg hole therein;

FIG. 5 is a view similar to FIG. 4, illustrating an alternate multidirectional peg for use in accord with the system of the invention;

FIG. 6 is a perspective view of the multidirectional peg shown in FIG. 5;

FIG. 7 is a broken longitudinal section view across line 7—7 in FIG. 6;

DETAILED DESCRIPTION OF THE PREFERRED EMBODIMENTS

Figure 4:
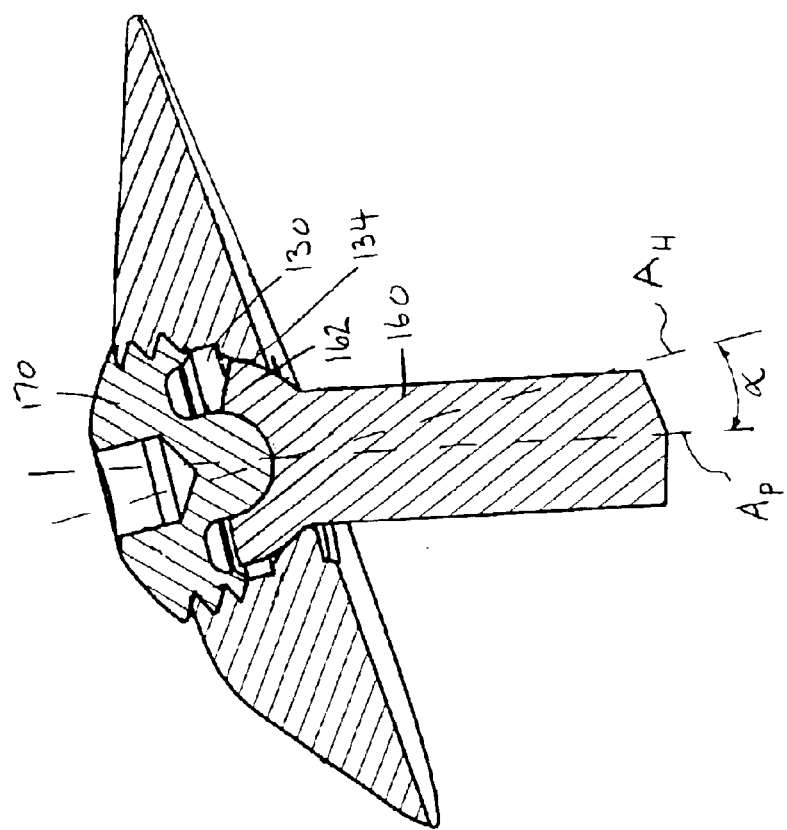
FIG. 4 is a view similar to FIG. 3, in which a multidirectional peg is angled relative to the orientation of the peg in FIG. 3.

Turning now to FIG. 1, a fracture fixation system 100 according to the invention is shown. According to a first embodiment of the system 100, the system is particularly adapted for aligning and stabilizing multiple bone fragments in a Colles' fracture. However, as discussed further below, the preferred aspects of the invention are applicable to numerous other fractures fixation systems adapted to align and stabilize other bone fractures, and particularly fractures occurring at or adjacent the metaphyseal portion of long bones.

According the first embodiment, the system 100 generally includes a substantially rigid T-shaped plate 102, commonly called a volar plate. Such a plate is intended to be positioned against the volar side of a fractured radial bone. The T-shaped plate 102 defines a head portion 116, and an elongate body portion 118 preferably angled relative to the head portion. The angle between the head portion 116 and the body portion 118 is preferably approximately 23° and bent at a radius of preferably approximately 0.781 inch. The distal edge 121 of the head portion 116 is preferably angled proximally toward the medial side at an angle, e.g. 5°, relative to a line that is perpendicular to the body portion 118. The plate 102 has a thickness of preferably approximately 0.1 inch, and is preferably made from a titanium alloy, such as Ti-6A-4V.

The body portion 118 includes four preferably countersunk screw holes 124, 126, 127, 128 for the extension of bone screws 104 therethrough. One of the screw holes, 128, is preferably generally oval in shape permitting longitudinal movement relative to the shaft of bone screw.

The head portion 116 includes four peg holes 130, preferably closely spaced (e.g., within 0.25 inch of each other) and preferably arranged along a line or a curve, for individually receiving pegs, discussed in detail below, therethrough. Referring to FIG. 2, the peg holes 130 include an upper internally threaded portion 132, and a lower spherically concave surface 134. Each peg hole defines its own axis $A_H$, and axes through the plurality of peg holes may extend parallel to or obliquely relative to each other.

In accord with the invention, two types of pegs are provided for insertion through the threaded peg holes, and both types of pegs can be used in any of the peg holes 130.

Still referring to FIG. 2, the first type of peg 140 includes a head 142 and a shaft 144. The head 142 has an upper externally threaded portion 146 adapted to engage the threads 132 of the holes 130, a lower spherically convex portion 148 adapted to seat against the concave surface 134 of the peg holes, and a driver receiving means, such as a proximal hex socket 150. The shaft 144 is preferably nonthreaded, as the pegs when inserted through the peg holes and coupled to the plate are adapted to provide a supporting framework about which bone fragments of the fracture can heal, but are not necessarily intended to provide a compressive force to the fragments. Alternatively, the shaft 144 may be threaded for an application in which positive engagement between the peg and bone is desired. Peg 140, when threadably engaged within any of the respective peg holes 130 of the plate 102, has an axis $A_P$ that extends in alignment with the axis $A_H$ of the respective peg hole.

Figure 3:
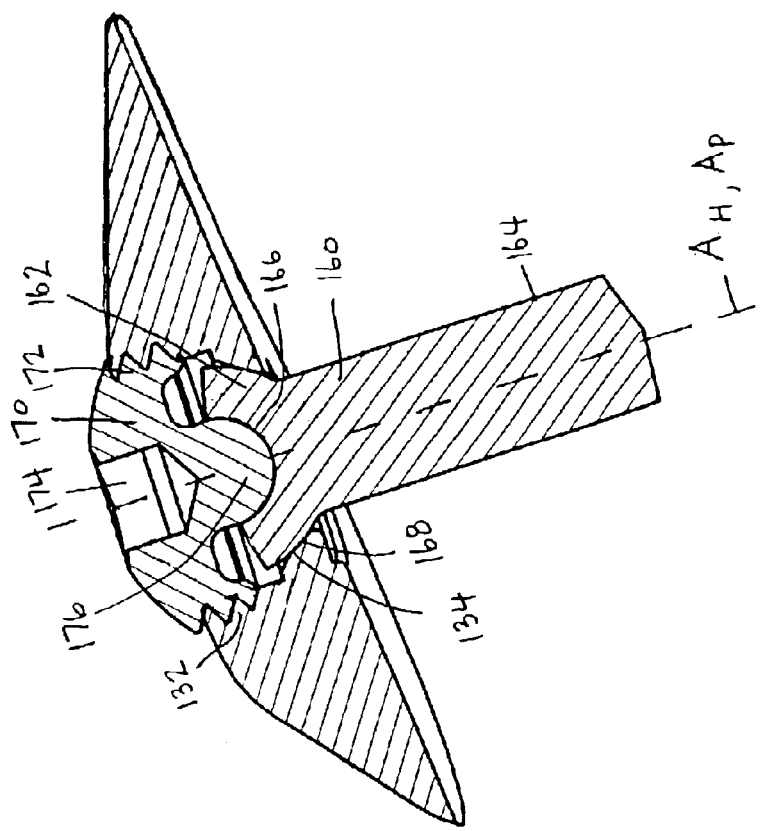
FIG. 3 is a section view of a head portion of the volar fixation system according to the invention, showing a multidirectional peg inserted in a peg hole therein.

Referring to FIG. 3, the second type of peg 160 includes a head portion 162 and a shaft 164. The head portion 162 defines an upper cup 166 (concave receiving surface) and an outer spherically convex portion 168. The spherically convex portion 168 has a radius of curvature that substantially corresponds with the radius of curvature of surface 134 about each peg hole. Surface 134 about the peg hole, and/or the convex portion 168 of the peg are preferably roughened, e.g., by electrical, mechanical, or chemical abrasion, or by the application of a coating or material having a high coefficient of friction.

Figure 3B:
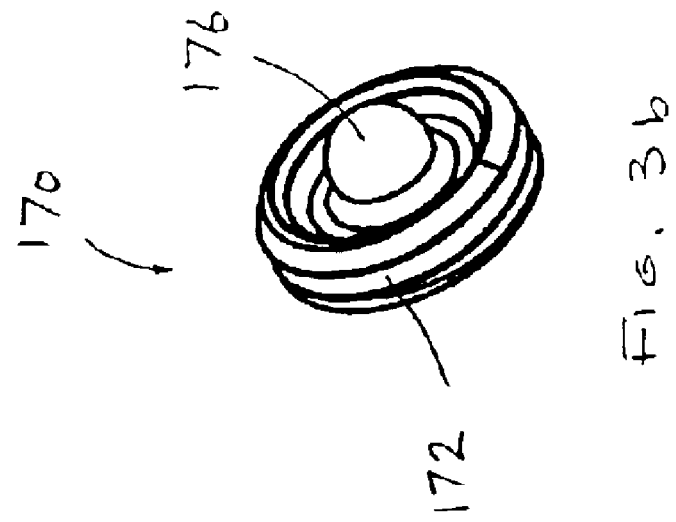
FIG. 3b is a bottom perspective view of a cap for the peg shown in FIG. 3.
Figure 3A:
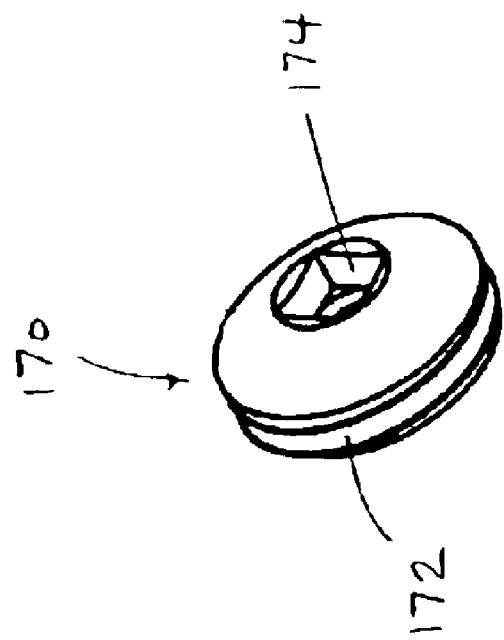
FIG. 3a is a top perspective view of a cap for the peg shown in FIG. 3.

Referring to FIGS. 3, 3a, and 3b, peg 160 is adapted to operate in conjunction with a cap 170 having an externally threaded portion 172 adapted to engage within the threaded portion 132 of a peg hole 130, a driver receiving means 174, and a lower preferably spherically curved ball portion (or nub) 176 sized to be at least partially received within the concave upper cup 166 of the peg 160.

Referring to FIG. 4, peg 160 can be inserted through any of peg holes 130 and infinitely adjusted such that an axis $A_P$ of the peg may be oriented at any angle α within a range of angles (e.g., ±15°) relative to axis $A_H$ defined by the peg hole. The cap 170 is then inserted into the peg hole 130 and tightened to clamp the head portion 162 of the peg 160 between the cap 170 and the lower spherically concave surface 134 surrounding the peg hole. As such, peg 160 can be independently fixed in an orientation selectable by the surgeon; i.e., the peg is multidirectional.

More particularly, and referring now to FIGS. 1 through 4, in use, the plate 102 is brought against the bone and aligned with the fracture such that the peg holes are situated substantially over the bone fragment or fragments. A first screw hole is drilled by the surgeon through hole 128 and into the radius bone. A first bone screw 104 is then inserted through the hole 128 in the plate 102 and secured to the bone. Prior to fully tightening the first bone screw 104 against the plate, the plate may be longitudinally adjusted relative to the screw. Once the proper position is established, the first screw can be tightened, and additional screws 104 may be inserted through the other screw holes 124, 126, 127 in a like manner.

The fractured bones are adjusted under the plate 102 into their desired positions for healing. The surgeon then drills holes into the bone for the pegs. The drilled holes may either be axial (i.e., parallel to the respective $A_H$ of the peg holes) or angled relative to the axes of the respective peg holes. The holes may be drilled in any direction within the permissible range of angles relative to the axes $A_H$ through the peg holes in accord with the treatment designed by the surgeon. Such holes may be drilled freehand, or may be assisted by a drill guide (not shown) that limits the relative angle of the drilled holes to be within the acceptable range of angles.

After each hole is drilled through a respective peg hole and into the bone, one of the first or second types of pegs 140, 160 is inserted through the peg hole in the plate and into the drilled hole. For a peg hole drilled axial with the axis $A_H$ of the peg hole, either of pegs 140 or 160 may be used. If the peg is of type 140, the shaft 144 of the peg is inserted through the peg hole 130 and into the drilled hole, and the peg is simply rotated about its axis to couple the head 142 of the peg to the plate 102. If the peg is of type 160, the peg is inserted through the peg hole and into the drilled hole, and the cap 170 is inserted over the head 162 of the peg and into the peg hole and then tightened to clamp the peg 160 in axial position.

For each hole that is drilled into bone at an angle relative to the direction of the axis $A_H$, a peg of type 160 is inserted through the peg hole 130 into the bone, and then retained with a cap 170, as discussed above.

Each hole may be drilled at the same angle as the others or at relatively different angles, depending upon the circumstances of the fracture being treated and the surgeon's treatment plan. In most cases, the preferred supporting framework for the pegs 140, 160 will indicate pegs that extend in a plurality of oblique directions such that, even though the shafts of the pegs are preferably non-threaded, the pegs once inserted in the holes operate to lock the bone fragment or fragments relative to the plate 102.

Turning now to FIGS. 5, 6 and 7, a first alternate multidirectional peg 160a for use in the above described system is shown. Peg 160a includes a head portion 162a defining an upper cup 166a including substantially spherically-curved concave surfaces 165a, and a Philips slot 167a. The head portion 162a also includes an outer spherically convex portion 168a. The peg 160a also includes a shaft 164a, which may be threaded or non-threaded. The peg 160a is utilized in conjunction with cap 170. In the first alternate embodiment, the peg 160a may be inserted through a peg hole in a fixation device and into a hole drilled in bone with the aid of an instrument having a Philips driver. The Philips driver is received in the Philips slot 167a, and rotational force is provided to the peg. The rotational force facilitates insertion of the shaft 164a of the peg 160a into a drilled hole, even where the shaft is non-threaded.

Figure 9:
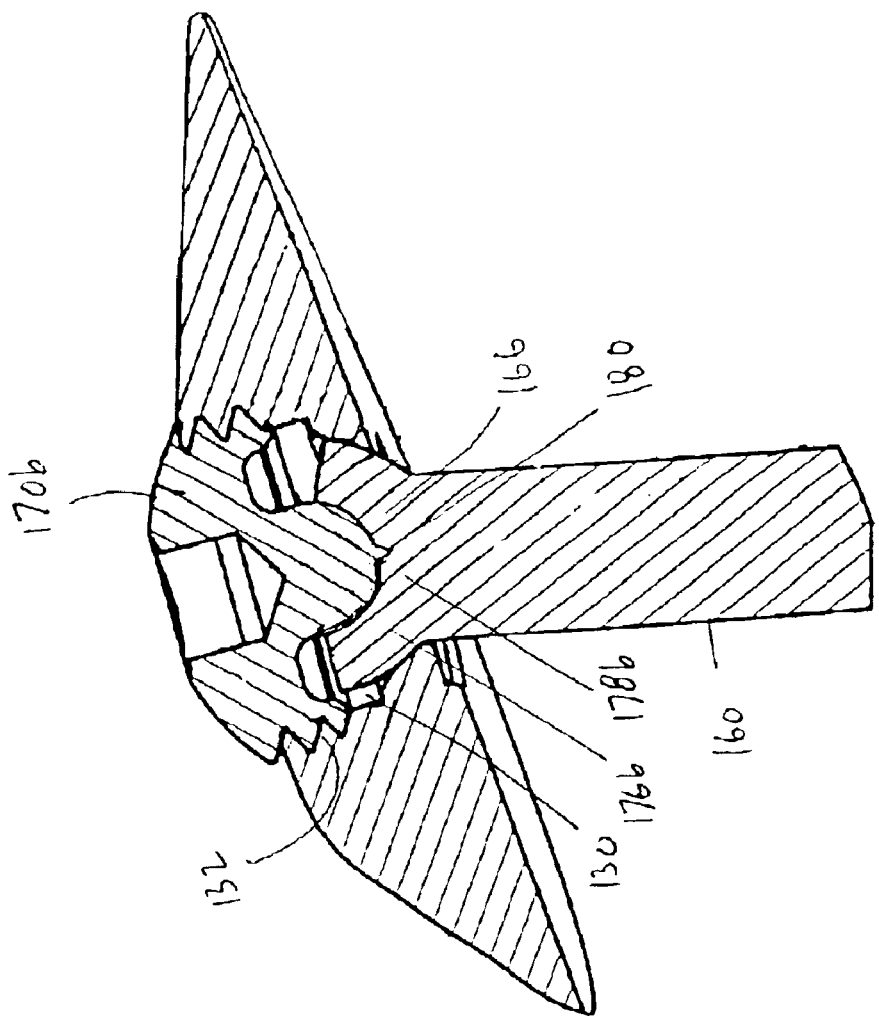
FIG. 9 is a view similar to FIG. 4 showing the cap of FIG. 8 in use.
Figure 8:
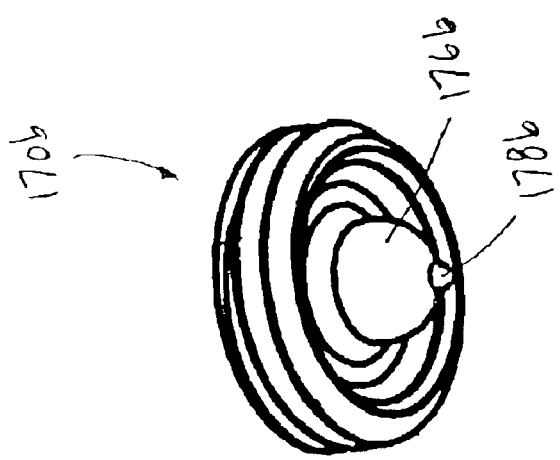
FIG. 8 is a bottom perspective view of a first alternate cap for a multidirectional peg.

Referring now to FIGS. 8 and 9, a first alternate embodiment of a cap 170b for a multidirectional peg is shown. The cap 170b includes a point 178b (e.g., a conical, frustoconical, cylindrical, or other shaped protuberance) extending from the spherically curved ball portion (or nub) 176b at the center of rotation thereof. The point 178b or the entirety of the cap 170b is preferably made from a material harder than the material of the peg 160. The point 178b is adapted to make a substantially point-to-surface contact 180 with the surface of the cup 166 of the peg when the cap is threaded into the upper portion 132 of the peg hole 130 of the fixation device having a peg received therein. As the area being contacted is greatly reduced, the force at the point of contact is substantially increased, thereby enhancing the stability of the peg.

Figure 10:
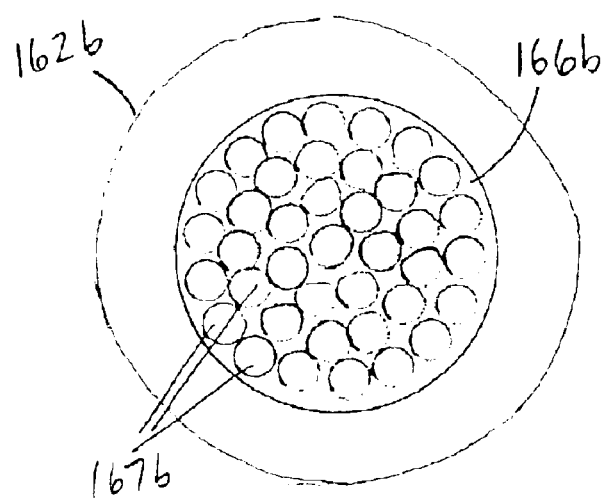
FIG. 10 is a top view of a multidirectional peg provided with engagement structure.
Figure 11:
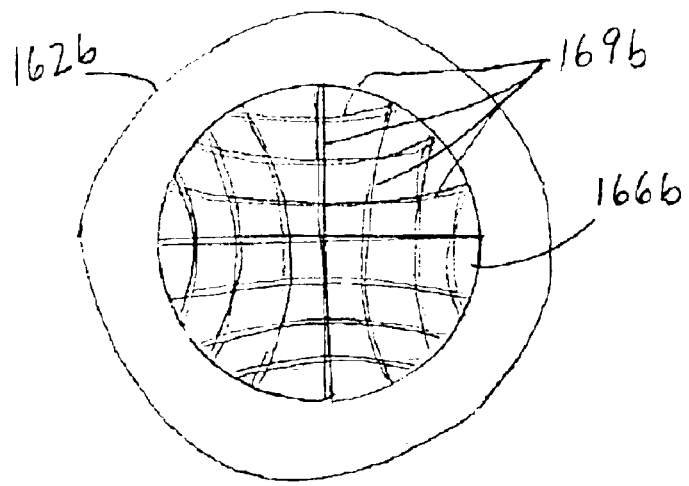
FIG. 11 is a top view of a multidirectional peg provided with other engagement structure.

Referring to FIGS. 10 and 11, as an alternate to a smooth cup surface, the cup 166b at the head 162b of the peg can optionally be provided with structure to aid engagement of the cup 166b by the point 178b of the cap 170b so at to fix the peg in an angular orientation. Such structure may include the formation of a plurality of compartments defined, e.g., by a plurality of wells 167b (FIG. 10) or an orthogonal (or honeycomb) arrangement of walls 169b (FIG. 11). Then, when the cap is inserted into the peg hole, the point 178b engages with the structure, e.g., enters into a well or a location between walls on the surface, to positively fix the peg in a particular angular orientation.

Figure 13:
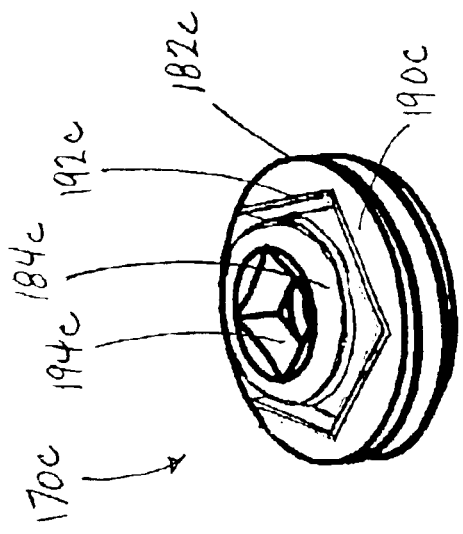
FIG. 13 is a top perspective view of the cap of FIG. 12.
Figure 12:
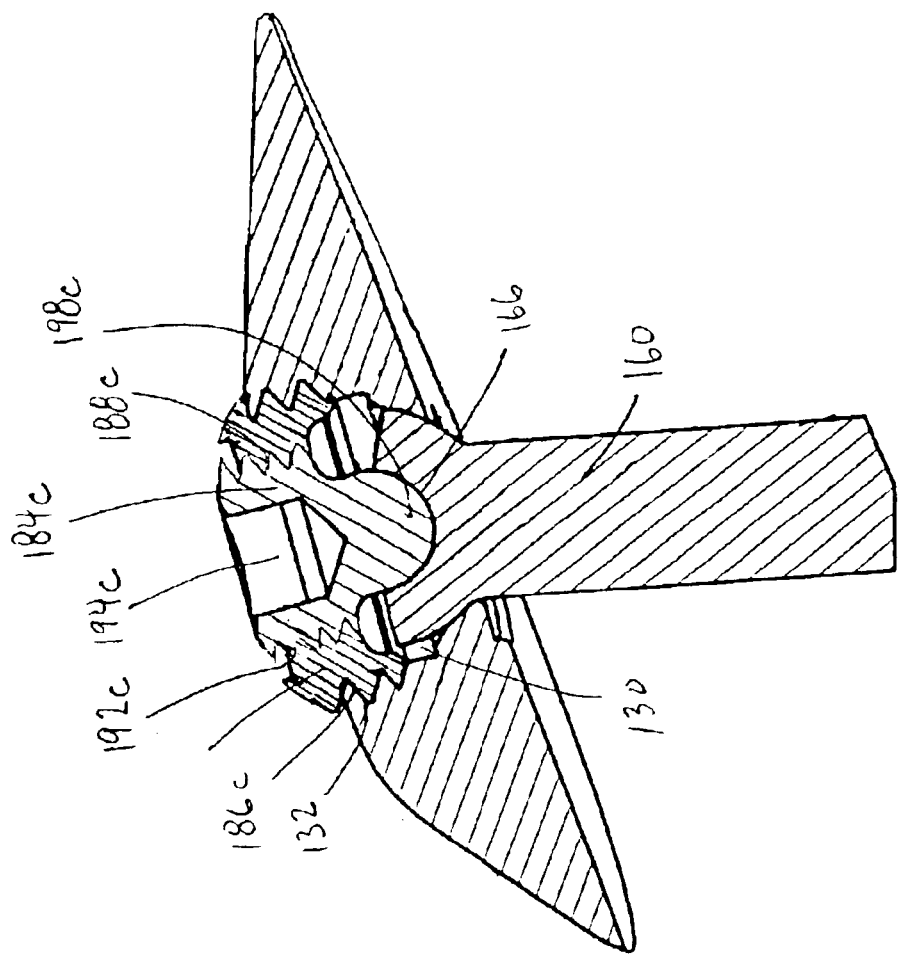
FIG. 12 is a view similar to FIG. 4 showing a second alternate cap for a multidirectional peg.

Turning now to FIGS. 12 and 13, a second alternate embodiment of a cap 170c for a multidirectional peg 160 is shown. The cap 170c comprises two parts: a base 182c and a set screw 184c. The base 182c has a diameter and threads 186c such that it is adapted to be threadably received into the threaded upper portion 132 of a peg hole 130. The base 182c also includes a bore (defined at the location of set screw 184c) with internal threads 188c, preferably of a smaller pitch (i.e., a relatively greater number of threads per inch) than threads 186c. The upper side 190c of the base 182c includes a recess 192c adapted to receive a driver for rotational driving the base. The recess 192c can have a hexagonal shape (as shown) or be provided in any other non-circular shape than can be defined about the bore. The set screw 184c includes an upper square recess 194c for receiving a rotational driver, external threads 196c corresponding to internal threads 188c, and a lower spherical nub 198c.

In use, after a multidirectional peg 160 is inserted through a peg hole 130 of a fixation device, the base 182c is rotationally inserted into the upper portion 132 of the peg hole 130. It is noted that rotation of the base 182c is subject to little resistance, as even fully seating the base will not cause any portion of the base to contact the head of the peg. After the base 182c is fully seated, the set screw 184c is rotationally driven into the threaded bore of the base. The set screw 184c is inserted until the nub 198c contacts the cup 166 of the peg 160 and places thereon a force sufficient to stabilize the peg. As the set screw is rotated on relatively smaller threads, greater mechanical advantage is provided and thus significant frictional force can be effected between the set screw 184c and the cup 166.

The above described system allowing the use of common peg holes to receive either a peg at a fixed direction or a multidirectional peg is adaptable to substantially any fixation system that uses pegs.

Figure 14:
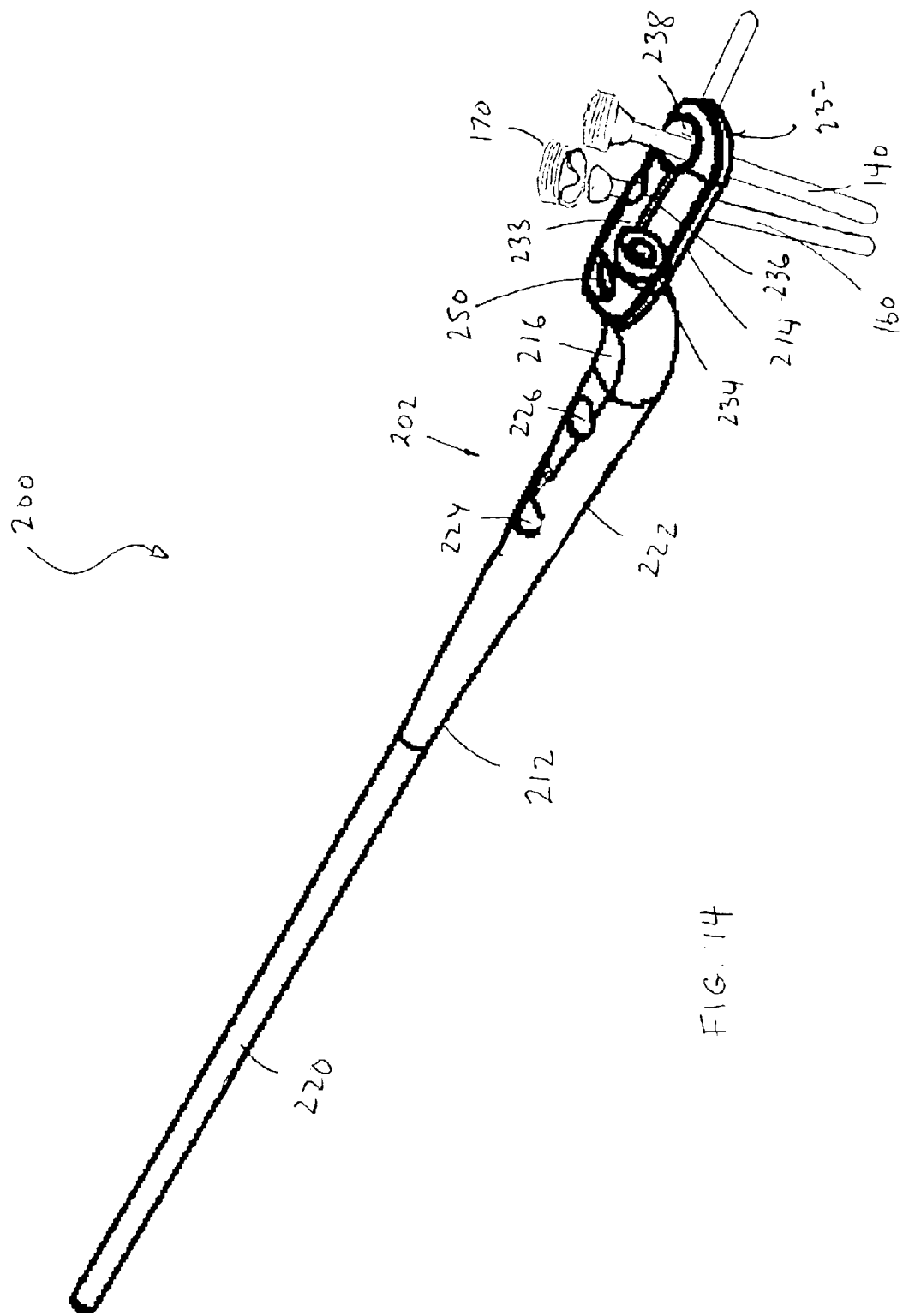
FIG. 14 is a perspective view of a nail-plate device provided with both unidirectional and multidirectional pegs in accord with the invention.

For example, turning now to FIG. 14, a nail-plate system 200 is shown. Nail-plates are suitable for fixation of fractures at the ends of long bones (metaphyseal fractures), such as the radius, the ulna, the femur, and the tibia, with the device and pegs provided in a size suitable for the bone for which the device is to be used. The nail-plate system 200 includes a device 202 having a proximal nail portion 212 and a plate portion 214 that is preferably horizontally and vertically offset relative to the nail portion, e.g., by a curvilinear neck portion (or transition zone) 216. As such, the nail portion 212 and the plate portion 214 are preferably fixed in a parallel, but non-coaxial relationship.

The nail portion 212 is preferably substantially circular in cross section and includes a resilient section 220, and a tapered relatively rigid section 222 generally substantially larger in diameter. The rigid section 222 of the nail portion 212 preferably includes two cortical screw holes 224, 226 arranged along the length of the rigid section 222 and adapted to receive cortical screws.

The plate portion 214 is substantially rigid and has a low and narrow profile. The plate portion 214 has a preferably slightly concave bottom surface 232 and a preferably slightly convex upper surface 233. The plate portion 214 preferably includes a screw hole 250 adjacent or in the neck portion 216 that is adapted to receive a stabilization screw. The plate portion 214 also includes one or more, and preferably three longitudinally displaced, threaded peg holes 234, 236, 238, each of which includes an upper threaded portion and a lower spherical concave portion, as discussed above with respect to peg holes 130 (see FIG. 2). The axes of the peg holes 234, 236, 238 may be parallel or oblique relative to each other. Regardless, the exact orientation of pegs placed through the peg holes may be adjusted (within a range of angles) by the use of all multidirectional pegs, such as peg 160 (and the associated cap 170), or with a combination of fixed-direction and multidirectional pegs 140, 160, in the manner described above with respect to the volar plate system 100. The implantation of the nail-plate is discussed in detail in previously incorporated, co-owned U.S. Ser. No. 10/159,611, filed May 30, 2002.

Figure 15:
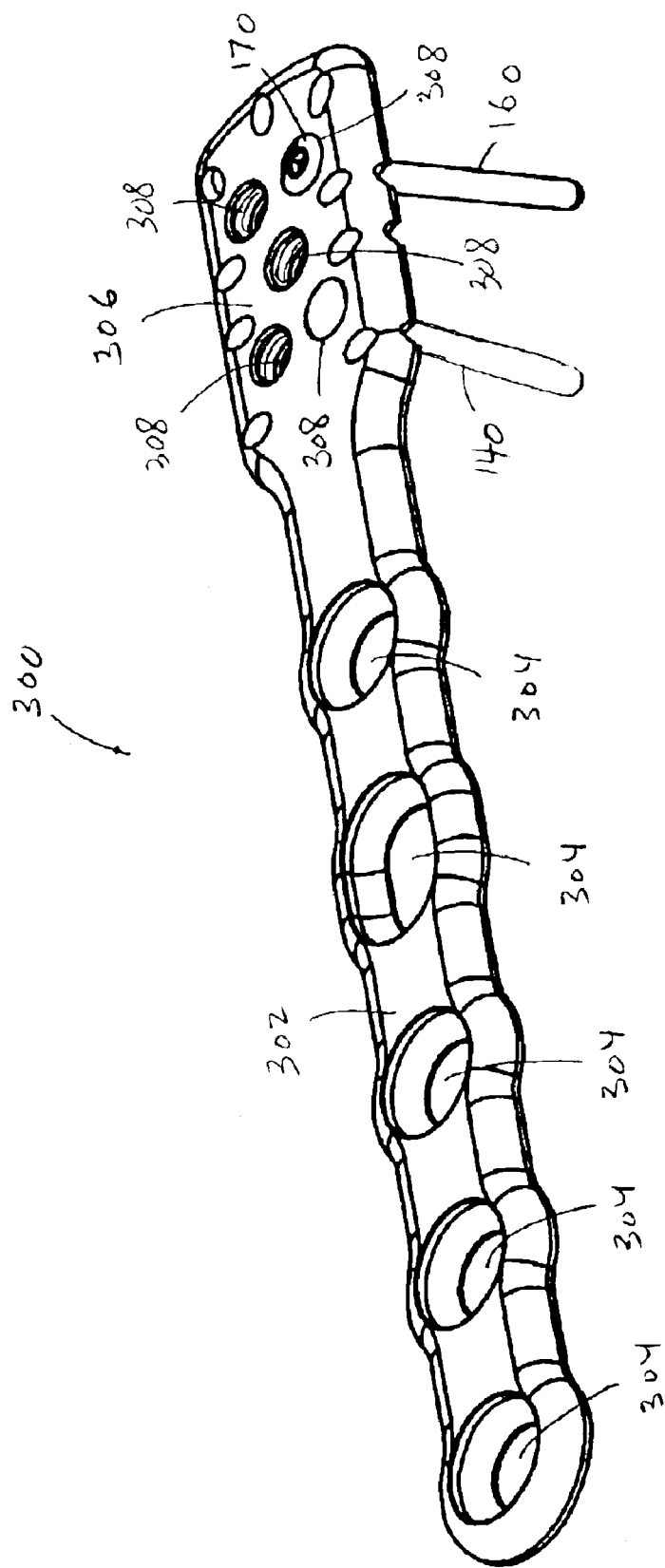
FIG. 15 is a perspective view of a humeral plate provided with both unidirectional and multidirectional pegs in accord with the invention.

Turning now to FIG. 15, a humeral plate system 300 is shown for fixation of a humeral fracture. The humeral plate 300 is an elongate plate having a body portion 302 with a plurality of screw holes 304, and a head portion 306 with a plurality of peg holes 308, similar in design to peg holes 130 (FIG. 2). Pegs 140 (FIG. 2) and pegs 160 (FIGS. 3 and 4) and 160a (FIG. 6) and a cap therefor 170 (FIGS. 3a and 3b), 170b (FIG. 8), or 170c (FIG. 13) can be used in the peg holes in the manner described above.

There have been described and illustrated herein several embodiments of fracture fixation systems having threaded peg holes adapted to individually receive both unidirectional (fixed angle) and multidirectional (or directable) pegs. In the directable peg embodiment, the head of a peg is preferably clamped between a portion of the fixation plate and a discrete cap, preferably with the head of the peg and fixation plate thereabout being treated to have, or having as material properties, high friction surfaces to enhance the fixation of the peg. Alternatively, the cup of the peg may have structure to adapted to receive and capture a portion of the cap. In the unidirectional embodiment, the lower portion of the head of the peg is shaped in accord with a peg hole structure adapted for the directable peg. While particular embodiments of the invention have been described, it is not intended that the invention be limited thereto, as it is intended that the invention be as broad in scope as the art will allow and that the specification be read likewise. Thus, while exemplar devices have been discussed, it is not intended that such discussion define a limitation to the claims. Other bone fixation devices, for example and not by way of limitation, such as spinal fixators, are also within the intended scope. Also, while particular materials for the elements of the system have been disclosed, it will be appreciated that other materials may be used as well. In addition, fewer or more peg holes and pegs may be used, preferably such that at least two pegs angled relative to each other are provided. Also, while it is disclosed that the pegs may be directed through a range of 15°, the peg holes and the heads of the pegs may be modified to permit a greater, e.g. up to 30°, or smaller, e.g. 5°, range of such angular direction. Furthermore, while a hex slot is disclosed on both the head of the fixed angle peg and the cap for receiving a driver to applying rotational force to the peg and cap, it will be appreciated that other rotational engagement means, e.g., a square, a Phillips, slotted, star, multi-pin, or other configuration may be used. Also, the device and pegs may be provided in different sizes adapted for implant into different size people. Furthermore, while some elements have been described with respect to the mathematically defined shapes to which they correspond (e.g., spherical), it is appreciated that such elements need only correspond to such shapes within the tolerances required to permit the elements to adequately function together; i.e., the elements may be only "substantially" spherical in curvature such that the elements can rotate relative to one another and be securely clamped. Furthermore, where parts are intended to rotate relative to each other, it is appreciated, although less preferred, that the parts may together define sufficient space therebetween permitting such rotation even if surface-to-surface contact is not maintained along the facing portions of the relevant parts. Moreover, various aspects of the several embodiments can be combined in yet other embodiment. For example, the set screw of a two-part cap can be provided with a point on its ball portion adapted to engage the cup of a peg. It will therefore be appreciated by those skilled in the art that yet other modifications could be made to the provided invention without deviating from its spirit and scope as claimed.

What is claimed is:

1. A peg for use in a threaded peg hole in a fracture fixation device, comprising:

a head and a non-threaded shaft, said head including a proximal portion having an external thread, a distal portion having a substantially spherically convex surface, and means for receiving a rotational driver.

2. A peg system for use in a fracture fixation device, comprising:

a) a peg having a non-threaded head and a non-threaded shaft, said head defining a proximal cup provided with means for receiving a rotational driver and a distal portion having a substantially spherically convex surface; and b) a cap having an external thread, means for receiving a rotational driver, and a protuberance adapted to engage within said proximal cup of said peg.

3. A kit for a fracture fixation system, comprising:

a) a fracture fixation device defining at least first and second like peg holes, each said peg hole having an upper portion provided with an internal thread;

b) a first peg couplable within at least said first peg hole, said first peg having a head and a shaft, said head having an external thread engageable with said internal thread, means for receiving a rotational driver;

c) a second peg couplable within at least said second peg hole, said second peg having a head and a shaft; and d) a cap having an external thread that is engageable with said internal thread of said second peg hole and means for receiving a rotational driver.

4. A kit according to claim 3, wherein:

said cap includes an element for engagement with said head of said second peg to angularly fix said head of said second peg within said second peg hole.

5. A kit according to claim 4, wherein:
said element is adapted to clamp against said head of said second peg to provide said angular fixation.

6. A kit according to claim 4, wherein:
said head of said second peg includes a cup having a surface area, and said element of said cap includes a protuberance adapted to define a substantially small contact area relative to said surface area of said cup.

7. A kit according to claim 4, wherein:
said cap comprises a base and a set screw,
said base includes said external thread adapted to thread with said internal thread of said first and second peg holes an internal thread, and said means for receiving a rotational driver, and
said set screw includes an external thread adapted to thread with said internal thread of said base, a second means for receiving a rotational driver, and said element.

8. A kit according to claim 7, wherein:
said external thread of said base has a first pitch, said external thread of said set screw has a second pitch, and said first pitch is greater than said second pitch.

9. A kit according to claim 3, wherein:
said head of said second peg defines a cup having means for receiving a rotational driver.

10. A kit according to claim 4, wherein:
said head of said second peg defines a concave surface, and said element has a spherically-curved convex surface corresponding to said concave surface.

11. A kit according to claim 3, wherein:
said first peg hole includes a lower portion having a substantially spherically concave surface, said first peg includes a portion having a substantially spherically convex surface corresponding to said spherically concave surface, said substantially spherically concave surface and said substantially spherically convex portion intended for contact with each other.

12. A kit according to claim 3, wherein:
said shaft of said first peg is non-threaded.

13. A kit according to claim 3, wherein:
said shaft of said second peg is non-threaded.

14. A kit according to claim 13, wherein:
said second peg includes means for receiving a rotational driver.

15. A kit according to claim 3, wherein:
said fixation device is a plate.

16. A kit according to claim 3, wherein:
said fixation device is nail-plate.

17. A kit according to claim 3, wherein:
when said first and second pegs are fixed within said at least first and second peg holes, said first and second pegs are collectively oriented to provide a framework for supporting fractured bone fragments, said first and second pegs of said framework defining a plurality of non-parallel axes.

18. A kit according to claim 3, wherein:
said at least first and second peg holes includes at least three peg holes closely spaced in a linear or curvilinear arrangement.

19. A kit according to claim 3, wherein:
said fixation device includes a plate portion defining said at least first and second peg holes.

20. A kit according to claim 19, wherein:
said plate portion has a body portion and a head portion angled relative said body portion, said head portion defining said at least first and second peg holes.

21. A kit according to claim 19, wherein:
said fixation device also includes a nail portion extending from said plate portion.

22. A kit according to claim 3, where
said fixation device includes at least one non-threaded screw hole.

23. A fracture fixation system, comprising:
a) a fracture fixation device defining at least one peg hole, said peg hole having an upper portion provided with an internal thread, and a lower portion having a substantially spherically concave surface;
b) a first peg having a head and a shaft, said head including a first portion having an external thread adapted to thread with said internal thread, a second portion having a substantially spherically convex surface corresponding to said substantially spherically concave surface, and means for receiving a rotational driver;
c) a second peg having a head and a shaft, said head including a first portion defining a cup and having a substantially spherically convex surface corresponding to said substantially spherically concave surface; and
d) a cap having an external thread adapted to thread with said internal thread, means for receiving a rotational driver, and an element sized to be received within said cup of said second peg.

24. A fracture fixation system according to claim 23, wherein:
at least one of said substantially spherically concave surface of said device, said substantially spherically convex surface of said first peg and said substantially spherically convex surface of said second peg is provided with a relatively high coefficient of friction.

25. A fracture fixation system according to claim 23, wherein:
one of said shaft of said first peg and said shaft of said second peg is non-threaded.

26. A fracture fixation system according to claim 23, wherein:
said fixation device is a plate device.

27. A fracture fixation system according to claim 26, wherein:
said plate device is a volar plate.

28. A fracture fixation system according to claim 23, wherein:
said fixation device is a nail-plate device.

29. A fracture fixation system according to claim 23, wherein:
said fixation device includes a plurality of peg holes.

30. A fracture fixation system according to claim 23, wherein:
said cup of said second peg includes a surface area, and said element of said cap includes a protuberance adapted to define a substantially small contact area relative to said surface area of said cup.

31. A fracture fixation system according to claim 23, wherein:
said a cap comprises a base and a set screw,
said base includes said external thread adapted to thread with said internal thread of said at least one peg hole, an internal thread, and said means for receiving a rotational driver, and
said set screw includes an external thread adapted to thread with said internal thread of said base, a second means for receiving a rotational driver, and said element.

32. A fracture fixation system according to claim 31, wherein:
said external thread of said base has a first pitch, said external thread of said set screw has a second pitch, and said first pitch is greater than said second pitch.

33. A fracture fixation system according to claim 23, wherein:
said cup of said second peg defines means for receiving a rotational driver.

34. A fracture fixation system according to claim 23, wherein:
said at least one peg hole includes first and second peg holes, said first peg hole defines a first axis and said second peg hole defines a second axis,
wherein said first peg is coupled within said first peg hole in alignment with said first axis, and said second peg is coupled within said second peg hole at an angle relative to said second axis.

35. A fracture fixation system according to claim 34, wherein:
said first and second axes are parallel.

36. A fracture fixation system according to claim 34, wherein:
said angle is within a range of ±15° relative to said second axis.

37. A method of treating a bone fracture, comprising:
a) providing a fixation device having a plurality of like threaded peg holes, each of said peg holes defining an axis, having an upper portion provided with an internal thread, and a lower portion having a substantially spherically concave surface;
b) positioning the fixation device over the bone fracture;
c) drilling holes through the peg holes into the bone, wherein a first of the drilled holes is drilled substantially coaxial with the axis through a peg hole, and a second of the drilled holes is drilled at an angle relative to the axis through a peg hole;
d) providing a first peg having a head and a shaft, said head including an external thread adapted to thread with said internal thread, a portion having a substantially spherically convex surface corresponding to said substantially spherically concave surface, and means for receiving a rotational driver;
e) inserting said first peg through one of the peg holes such that the shaft of the first peg extends into the first drilled hole;
f) providing a second peg and a discrete cap, said second peg having a head and a shaft, said head of said second peg including a portion defining a cup and having a substantially spherically convex surface corresponding to said substantially spherically concave surface, and said cap having an external thread, means for receiving a rotational driver, and an element sized to be received within said cup of said second peg;
g) inserting the second peg through another of the peg holes such that the shaft of the second peg extends through the second drilled hole; and
h) threadably engaging the cap in the other of the peg holes until a portion of the cap engages the head of the second peg.

38. A method according to claim 37, wherein:
said threadably engaging the cap causes clamping of the head of the second peg between the cap and the fixation device.

39. A method according to claim 37, wherein:
said providing said second peg and a discrete cap includes providing said second peg with a non-threaded shaft.

* * * * *